United States Patent [19]

Ayroles et al.

[11] Patent Number: 4,981,688
[45] Date of Patent: Jan. 1, 1991

[54] **METHOD FOR OBTAINING AN EXTRACT OR *GINKGO BILOBA* LEAVES**

[75] Inventors: Georges Ayroles; René-Marc Rossard, both of Gaillac; Michel Cadiou, Castelnau-de-Montmiral, all of France

[73] Assignee: Pierre Fabre Medicament, Paris, France

[21] Appl. No.: 313,372

[22] Filed: Feb. 21, 1989

[30] Foreign Application Priority Data

Feb. 24, 1988 [FR] France ............................ 88 02227

[51] Int. Cl.$^5$ .............................................. A61K 35/78
[52] U.S. Cl. .................................................... 424/195.1
[58] Field of Search ...................................... 424/195.1

[56] References Cited

U.S. PATENT DOCUMENTS

| | | | |
|---|---|---|---|
| 4,564,477 | 1/1986 | Takigawa et al. | 568/410 X |
| 4,683,140 | 7/1987 | Kang | 424/195.1 X |
| 4,734,280 | 3/1988 | Braquet | 514/920 X |

FOREIGN PATENT DOCUMENTS

| | | |
|---|---|---|
| 0086315 | 8/1983 | European Pat. Off. . |
| 0237066 | 9/1987 | European Pat. Off. . |
| 2007352 | 1/1970 | France . |
| 2132761 | 11/1972 | France . |

OTHER PUBLICATIONS

Chemical Abstracts, vol. 101, (1984), p. 306, No. 60122e.
Chemical Abstracts, vol. 107, (1987), p. 324, No. 28395j.
Nakanishi, "The Ginkgolides", *Pure and Applied Chemistry*, 14, pp. 89–113 (1983).
Okabe, et al., "Ginkgolides", *J. Chem. Soc.* (C), pp. 2201–2206, (1967).

*Primary Examiner*—John W. Rollins
*Attorney, Agent, or Firm*—Ladas & Parry

[57] ABSTRACT

The present invention relates to a novel method for obtaining an extract of *Ginkgo biloba* leaves.

In the method according to the invention, the following successive operations are performed: grinding of the *Ginkgo biloba* leaves; extraction of the ground preparation of *Ginkgo biloba* leaves using an aqueous ketone solvent; concentration of the extraction liquors in order to precipitate the biflavonoids and the hydrophobic substances; filtration of the aqueous concentrate; alkalinization of the filtrate so as to precipitate the proanthocyanidins; removal by filtration of the insoluble fraction containing the proanthocyanidins; acidification of the filtrate; liquid-liquid extraction of the filtrate with a $C_4$–$C_6$ ketone in the presence of ammonium sulfate; and recovery of the extract by taking the ketone phase to dryness.

14 Claims, No Drawings

METHOD FOR OBTAINING AN EXTRACT OR *GINKGO BILOBA* LEAVES

The present invention relates to a method for obtaining an extract of Ginkgo biloba leaves, intended for administration orally or by injection for treating disorders of the arterial, capillary and venous circulation.

Extracts of Ginkgo biloba leaves have been used for a very long time in the treatment of disorders of the peripheral and cerebral circulation, especially in elderly people. The nature of the active substances present in these extracts, which are responsible for their venotropic activity, is also known (H. Peter, J. Fisel and W. Weisser: Pharmacologie des principes actifs de Ginkgo biloba (Pharmacology of the active principles of Ginkgo biloba), pages 719 –725, no. 6, 1966).

It has also been known for a long time that extracts of green leaves of Ginkgo biloba contain some constituents which cause various problems, in particular of toxicity, when these extracts are intended for administration by injection. The constituents in question are polyphenolic derivatives, generally designated by the name proanthocyanidins, especially prodelphinidins.

These problems are, in particular, described in the following publications:

R. HEMMER Arzneimittel Vorschung 17, 491 (1967)

K. WEINGES Arzneimittel Vorschung 18, 539 (1968)

K. WEINGES Arzneimittel Vorschung 19, 328 (1969)

Various solutions have been recommended hitherto for obtaining a Ginkgo biloba extract containing a low dose of proanthocyanidins. However, none of these solutions are completely satisfactory, either because the level of proanthocyanidins remains too high in the final extract, or else because the purification involves difficulties of implementation, in particular those resulting from the use of solvents, polymers or heavy metal derivatives which are generally toxic. Furthermore, it was observed that thorough removal of the proanthocyanidins generally brought about a concomitant reduction in the active substances of the Ginkgo biloba extract, especially the flavone glucosides, quercetin and kaempferol. Finally, the extraction yield was very unfavorably influenced by known treatments for removal of proanthocyanidins.

The present invention is directed precisely towards remedying all these drawbacks, by providing a method for obtaining an extract of Ginkgo biloba leaves which, furthermore, proves simpler to carry out and more economical.

According to the present invention, in the method for obtaining an extract of Ginkgo biloba leaves, the following successive operations are performed:

grinding of the Ginkgo biloba leaves, extraction of the ground preparation of Ginkgo biloba leaves using an aqueous ketone solvent, concentration of the extraction liquors in order to precipitate the biflavonoids and the hydrophobic substances, filtration of the aqueous concentrate, alkalinization of the filtrate so as to precipitate the proanthocyanidins, removal by filtration of the insoluble fraction containing the proanthocyanidins, acidification of the filtrate, liquid-liquid extraction of the filtrate with a $C_4$-$C_5$ ketone in the presence of ammonium sulfate, and recovery of the extract by taking the ketone phase to dryness.

According to this method, the proanthocyanidins are removed by precipitation after an alkalinization of the aqueous filtrate, followed by a filtration of the insoluble fraction. This alkalinization of the filtrate is advantageously carried out until a pH value above 8, and which can even reach much higher values, in the region of 14, is obtained.

The proanthocyanidins can be precipitated by alkalinization of the aqueous filtrate by means of ammonia solution, ammonia gas or other basic agents, such as alkali metal or alkaline earth metal hydroxides, in particular sodium and calcium hydroxides, or alternatively amines, in particular alkylamines.

After removal of the proanthocyanidines, an acidification of the filtrate must be performed, so as to re-create good conditions for performing the subsequent liquid-liquid extraction. This acidification is obtained satisfactorily in practice by adding sulfuric acid. The pH of the filtrate can be lowered in this way to a value in the region of 1.

According to a further additional characteristic of the present invention, after acidification, the filtrate is subjected to a liquid-liquid extraction in the presence of ammonium sulfate. By way of examples of $C_4$-$C_6$ ketones used for carrying out this liquid-liquid extraction, methyl ethyl ketone and methyl isobutyl ketone will be mentioned. These ketones may be used mixed with acetone until a $C_4$-$C_6$ ketone/acetone ratio of 50:50 is obtained.

According to a further additional characteristic of the present invention, after the liquid-liquid extraction, the organic phase is separated off and ammonium sulfate is added again thereto. The extract is then recovered by taking the ketone phase to dryness. This taking to dryness is obtained in a conventional way, for example by concentration followed by drying under vacuum.

According to a further characteristic of the method of the invention, the dry extract can be taken up with an alcohol, optionally aqueous, the insoluble fraction is then removed by filtration and the final extract is recovered by drying the alcoholic filtrate again.

The primary extraction of the ground preparation of Ginkgo biloba leaves is carried out using an aqueous ketone solvent. According to an advantageous variant of the method of the invention, the extraction of the ground preparation is obtained using an acetone/water mixture corresponding to proportions of between 80:20 and 60:40, and preferably of the order of 70:30, at a temperature of the order of 50 to 60° C.

The subject of the present invention also encompasses the extracts of Ginkgo biloba leaves obtained by carrying out the method described above, and especially the extracts intended for administration orally and by injection. As will become apparent in the subsequent part of the description, these extracts, obtained according to the method of the invention, display a very low titer of proanthocyanidins but retain, on the other hand, a suitable content of the desired active principles. In practice, extracts displaying acceptable titers of proanthocyanidins are readily obtained.

Other characteristics and advantages of the method according to the invention will become apparent on reading the detailed description, given below with reference to a particular example of embodiment.

EXAMPLE

Twice 800 g of ground green leaves of Ginkgo biloba are extracted in countercurrent fashion with twice 13.5 liters of an acetone/water (70:30) mixture. This first extraction is performed at a temperature of between approximately 50 and 60° C. A temperature of approximately 55° C. has been used quite satisfactorily in practice.

After separation of the residuum by filtration, the liquors are concentrated under reduced pressure to a volume of approximately 1.9 liters, and a separation of the precipitate is then performed by decantation followed by filtration.

Concentration under vacuum followed by separation of the precipitate by decantation and filtration constitutes a first stage of purification of the method according to the invention, during which biflavonoids and other hydrophobic substances are removed.

The filtrate is then treated with ammonia solution so as to adjust the pH to approximately 9. A precipitation of the proanthocyanidins is thereby obtained. The insoluble fraction which precipitates is then filtered for the purpose of removing the proanthocyanidins.

Alkalinization of the filtrate followed by filtration of the proanthocyanidins constitutes the second essential stage of purification of the method according to the invention.

The pH of the filtrate is then adjusted by acidification using sulfuric acid to bring the pH of the filtrate back to a value in the region of 2. The filtrate is then extracted with approximately 1.250 liter of a butanone/acetone (70:30) mixture in the presence of approximately 650 g of ammonium sulfate.

The organic phase obtained during this liquid-liquid extraction is then treated with an additional approximately 200 g of ammonium sulfate, and thereafter filtered, concentrated and taken to dryness under reduced pressure.

This dry extract is then taken up in 8 volumes of aqueous ethanol, and thereafter washed with a further 2 volumes of aqueous ethanol. The suspension thereby obtained is then filtered so as to remove the insoluble fraction therefrom. The final extract is thereby recovered by concentrating the alcoholic filtrate and taking it to dryness under reduced pressure. The yield by weight is 90%.

Analysis of the extract thereby obtained gives the following assay:

| | |
|---|---|
| Proanthocyanidins | 6.46% |
| Flavone glucosides | 25.5% |
| Quercetin + kaempferol | 6.6% |

By way of comparison, an aliquot of the clarified aqueous concentrate derived from the first stage of purification was treated according to a customary process, that is to say without precipitation of the proanthocyanidins by alkalinization of the filtrate. This Ginkgo biloba extract assays as follows:

| | |
|---|---|
| Proanthocyanidins | 35.2% |
| Flavone glucosides | 24.5% |
| Quercetin + kaempferol | 6.3% |

Various experiments were performed, modifying the nature of the agent for alkalinization of the filtrate, necessary for precipitation of the proanthocyanidins during the second stage of purification of the method according to the invention. By way of example, the composition of the different extracts all obtained from batches of green leaves of the same quality is shown below in Table I.

TABLE I

| Removal of the proanthocyanidins | Proanthocyanidins % by weight | Flavone glucosides % by weight | Quercetin + kaempferol % by weight |
|---|---|---|---|
| Absence of alkalinization | 35.2 | 24.5 | 6.3 |
| Ammonia solution | 6.46 | 25.5 | 6.6 |
| Calcium hydroxide | 1.2 | 21.3 | 5.3 |
| Sodium hydroxide | 16.2 | 22.8 | 6.4 |
| Diethylamine | 7.0 | 25.5 | 7.3 |

Several extracts of Ginkgo biloba leaves possessing different contents of proanthocyanidins were subjected to a study of acute toxicity in mice, the extracts being administered by injections.

The administration was performed on batches of 10 mice. The extract was dissolved in 10% strength acetamide in water and administered in a volume of 50 ml/kg.

The results, read at T+7 days, are recorded in Table II below.

TABLE II

| PROANTHOCYANIDINS IN THE EXTRACT % by weight | $LD_{50}$ |
|---|---|
| 5.4% | approx. 1500 mg/kg |
| 18.5% | approx. 800 mg/kg |
| 30% | approx. 600 mg/kg |
| 59.6% | approx. 300 mg/kg |

We claim:

1. A process for obtaining an extract Ginkgo biloba leaves wherein the following successive operations are performed:
   grinding the Ginkgo biloba leaves,
   extraction of the ground preparation of Ginkgo biloba leaves using an aqueous ketone solvent,
   concentration of the extraction liquors in order to precipitate the biflavonoids and the hydrophobic substances,
   filtration of the aqueous concentrate,
   alkalinization of the filtrate to a pH of at least 8 by addition of alkali metal or alkaline earth metal hydroxides, ammonia gas or an amine so as to precipitate the proanthocyanidins,
   removal by filtration of the insoluble faction containing the proanthocyanidins,
   acidification of the filtrate,
   liquid-liquid extraction of the filtrate with a $C_4$-$C_8$ ketone in the presence of ammonium sulfate, and
   recovery of the extract by taking the ketone phase to dryness.

2. The process as claimed in claim 1 wherein the acidification of the filtrate, after removal of the insoluble fraction containing the proanthocyanidins, is carried out by means of sulfuric acid.

3. The process as claimed in claim 2, wherein said acidification is carried out until the pH is lowered to a value in the region of 1.

4. The process as claimed in claim 1 wherein, after acidification, the filtrate is subjected to a liquid-liquid extraction with methyl ethyl ketone in the presence of ammonium sulfate.

5. The process as claimed in claim 1 wherein, after acidification, the filtrate is subjected to a liquid-liquid extraction with methyl isobutyl ketone in the presence of ammonium sulfate.

6. The process as claimed in claim 1 wherein the $C_4$-$C_6$ ketone for liquid-liquid extraction is mixed with acetone.

7. The process as claimed in claim 6, wherein the $C_4$-$C_6$ ketone/acetone ratio can contain up to approximately 50% by volume of acetone.

8. The process as claimed in claim 1 wherein, after the liquid-liquid extraction, the organic phase is separated off and ammonium sulfate is added thereto.

9. The process as claimed in claim 1 wherein the taking of the ketone phase to dryness is carried out by concentration, followed by drying under vacuum.

10. The process as claimed in claim 1 wherein the dry extract obtained from the ketone phase is taken up with an alcohol, the insoluble fraction is then removed by filtration and the first extract is recovered by taking the alcoholic filtrate to dryness.

11. The process as claimed in claim 1 wherein the extraction of the ground preparation of Ginkgo biloba leaves is carried out using an acetone/water mixture in volume to volume proportions of between 80:20 and 60:40 at a temperature of about 50 to 60° C.

12. The process as claimed in claim 1 wherein the precipitation of the proanthocyanidins is obtained by alkalinization of the filtrate by means of an alkylamine.

13. A process according to claim 12 wherein the alcohol employed is an aqueous alcohol.

14. A process according to claim 13 wherein the acetone/water mixture employed has a volume/volume ration of about 70:30.

* * * * *

UNITED STATES PATENT AND TRADEMARK OFFICE
CERTIFICATE OF CORRECTION

PATENT NO. : 4,981,688

DATED : 1/1/91

INVENTOR(S) : Georges Ayroles, et al

It is certified that error appears in the above-identified patent and that said Letters Patent is hereby corrected as shown below:

On the title page, item [54], line 2, and column 1, line 1, in the title please delete "OR" and substitute --OF--.

Signed and Sealed this

Eighth Day of September, 1992

Attest:

DOUGLAS B. COMER

*Attesting Officer*     Acting Commissioner of Patents and Trademarks

UNITED STATES PATENT AND TRADEMARK OFFICE
CERTIFICATE OF CORRECTION

PATENT NO. : 4,981,688
DATED : 1/1/91
INVENTOR(S) : Georges Ayroles, et al

It is certified that error appears in the above-identified patent and that said Letters Patent is hereby corrected as shown below:

On the title page, item [54], line 2, and column 1, line 1, in the title please delete "OR" and substitute --OF--.

Signed and Sealed this

Seventeenth Day of August, 1993

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 4,981,688

DATED : JANUARY 1, 1991

INVENTOR(S) : George AYROLES, et al.

It is certified that error appears in the above-identified patent and that said Letters Patent is hereby corrected as shown below:

On title page, Item [73]

Assignee: "Medicament" should read -- Industrie --.

Signed and Sealed this

Third Day of May, 1994

Attest:

BRUCE LEHMAN

Attesting Officer                Commissioner of Patents and Trademarks